United States Patent [19]

Goel et al.

[11] Patent Number: 4,465,633

[45] Date of Patent: Aug. 14, 1984

[54] MANUFACTURE OF ARYL ESTERS

[75] Inventors: Anil B. Goel, Worthington; Peter E. Throckmorton, Plain City, both of Ohio

[73] Assignee: Ashland Oil, Inc., Ashland, Ky.

[21] Appl. No.: 441,360

[22] Filed: Nov. 15, 1982

[51] Int. Cl.$^3$ ................................................ C11C 3/02
[52] U.S. Cl. .............................. 260/410.9 R; 260/406; 260/410.5; 560/131
[58] Field of Search ............ 260/410.9 R, 406, 410.5; 560/131

[56] References Cited

U.S. PATENT DOCUMENTS

| | | | |
|---|---|---|---|
| 3,493,605 | 2/1970 | Selwitz | 260/410.5 |
| 3,646,111 | 2/1972 | Hörnig et al. | 560/131 |
| 3,651,127 | 3/1972 | Hörnig et al. | 560/131 |
| 3,772,383 | 11/1973 | Kominami et al. | 560/131 |
| 4,229,587 | 10/1980 | Murib | 560/131 |

*Primary Examiner*—Y. Harris-Smith
*Attorney, Agent, or Firm*—John F. Jones

[57] ABSTRACT

A process is described for the manufacture of aryl esters such as phenyl esters by liquid phase reaction of an aromatic compound such as benzene with molecular oxygen in the presence of a carboxylic acid preferably having 6 or more carbon atoms over a catalyst composed essentially of a compound of palladium, a compound of antimony and a compound of at least one member selected from the group consisting of chromium, cobalt, nickel, manganese, iron, and tin wherein the aromatic compound is added continuously to the reaction and water formed in the reaction is rapidly and continuously removed from the reaction zone.

10 Claims, No Drawings

MANUFACTURE OF ARYL ESTERS

CROSS-REFERENCE TO RELATED APPLICATIONS

This invention is an improvement over the process more fully described and claimed in copending U.S. patent application of Anil B. Goel and Robert A. Grimm, Ser. No. 348,561, filed Feb. 12, 1982. The use of a solvent in the production of aryl esters of higher aromatic hydrocarbons is disclosed and claimed in copending U.S. patent application Ser. No. 463,164, filed Feb. 2, 1982 by Anil B. Goel et. al.

BACKGROUND OF THE INVENTION

1. Field of the Invention

The present invention provides a process for making aryl esters from aromatic hydrocarbons such as benzene, naphthalene, anthracene, phenanthrene, biphenyl, terphenyls, and the like, which comprises reacting a mixture of the aromatic hydrocarbon, for instance benzene, a carboxylic acid, preferably one having at least 5 carbon atoms, and molecular oxygen in the liquid phase in the presence of a catalyst consisting essentially of palladium or a compound of palladium, a compound of antimony, and a compound of at least one member selected from the group consisting of chromium, cobalt, nickel, manganese, iron and tin. The use of a chromium compound in the catalyst, for instance, gives improved results over the process described and claimed in the copending U.S. pat. application of Anil B. Goel and Robert A. Grimm, Ser. No. 348,561 filed Feb. 12, 1982.

2. Description of the Prior Art

The manufacture of phenol by direct oxidation with oxygen is known. there are, for instance, thermal processes which are performed at very high temperatures in which the phenol formed is susceptible to further oxidation so that considerable loss of yield occurs as is disclosed in U.S. Pat. No. 2,223,383, in the presence of catalysts. The oxidation can be carried out at somewhat lower temperatures as in U.S. Pat. No. 3,133,122 but the reactions have been plagued by low conversions and excessive production of unwanted by-products as disclosed in U.S. Pat. No. 2,392,875.

It has already been proposed to make phenyl acetate and biphenyl from benzene and acetic acid in the liquid phase in the presence of palladium acetate and without added molecular oxygen by a Stoichiometric reaction in *Chem. and Ind.*, Mar. 12, 1966, page 457.

U.S. Pat. No. 3,542,852 discloses the preparation of hydroxy aromatic compounds by reaction of an aromatic compound and oxygen in the presence of a catalyst composed of iron, a noble metal or a compound of either in the presence of a nitrate ion and a carboxylic acid. More recently, the preparation of phenyl esters and phenols by the reaction of benzene, molecular oxygen and a lower aliphatic carboxylic acid in the presence of a catalyst composed of a Group VIII metal (U.S. Pat. No. 3,642,873) or a compound of such metal (U.S. Pat. No. 3,651,127) have been disclosed. Similarly, variations in this type of reaction have been disclosed in U.S. Pat. Nos. 3,646,111; 3,651,101; 3,772,383; 3,959,352 and 3,959,354. U.S. Pat. No. 3,959,354 concludes that liquid phase reactions of this type because of problems of catalyst elution, etc., are disadvantageous for an industrial process. U.S. Pat. No. 3,772,383 describes a liquid phase reaction using a very complex catalyst system which includes the use of nitric acid and a lower aliphatic carboxylic acid such as acetic, propionic, n-butyric, isobutyric or caproic acid. Generally speaking, these prior art processes deal for the most part with vapor phase oxidation reactions, or liquid phase reactions in which all the reactants (except oxygen in some instances) are initially included in the reaction mixtures, they use lower aliphatic carboxylic acids such as acetic and propionic acid, and they often require an alkali or alkaline earth metal carboxylate as part of the catalyst. Moreover, in general the prior art catalytic processes have produced very low conversions, usually less than 10%, with poor selectivity to the desired phenyl ester, and phenol is often a primary product of the oxidation reaction. The use of the lower saturated carboxylic acids, primarily acetic acid, in the prior art processes produce a highly corrosive system which can cause reaction equipment problems and excessive recycle costs as well as the poor conversions and selectivities mentioned above. None of the prior art processes disclose the continuous addition of benzene and the continuous removal of water from the reaction mixture as it forms.

SUMMARY OF THE INVENTION

We have discovered an oxidation process for the transformation of benzene, and similar aromatic compounds, molecular oxygen and a carboxylic acid to the corresponding aromatic carboxylate in high conversions and selectivities to the desired product. Our discovery is based to some extent on the use of a relatively higher boiling mono or poly-carboxylic acid such as lauric acid or dodecanedioic acid as the carboxylic acid reactant in our process. We have discovered that the use of carboxylic acids having 5 or more carbon atoms and a liquid reaction phase in our process as well as our palladium-antimony-chromium type of catalyst not only helps in dramatically increasing the conversion of benzene and increasing the selectivity to the phenyl carboxylate over that described in the prior art, but that these carboxylic acids are much less corrosive and much easier to recycle than are the lower aliphatic carboxylic acids disclosed for similar types of reactions in the prior art.

We have also discovered in contrast to what was previously known in the art that our catalyzed liquid phase reaction produces high conversions and quantitative yields of phenyl ester when benzene is continuously added to the reaction and water is continuously removed from the reaction as it forms during the entire course of the reaction. Excess amounts of benzene in the reaction mixture during the oxidation reaction as is shown in the prior art appear to be responsible for production of undesirable by-products such as biphenyl. Water can be conveniently removed in the case of benzene reactant by continuous removal of excess benzene by azeotropic distillation and removal of the water as it is formed in the reaction. If water, which is a by-product of the reaction, is allowed to remain in the reaction mixture it can cause hydrolysis of the phenyl carboxylate to form phenol which, in turn, can cause inactivation of the catalyst.

The catalysts of our processes are preferably composed of palladium metal or compound of palladium and usually a palladium carboxylate in conjunction with an antimony compound and a chromium compound and/or a compound of cobalt, nickle, manganese, iron or tin. The use of significant amounts of other materials such as those described as being catalyst promoters in the prior art in addition to the essential palladium, antimony and chromium or other designated metal compound components of our catalyst is usually detrimental to our process. The catalysts of this invention may be used alone or may be supported on a carrier or carriers. Suitable carriers include silica, alumina, carbon, quartz, pumice, diatomaceous earth, and the like and others which are well known in the art.

The carboxylic acids useful in our invention include mono and poly-carboxylic acids and preferably those having 5 or more carbon atoms which correspond to the formula $R(COOH)_n$ wherein n is an integer of 1 or more and R is a hydrocarbon group having at least 5-n carbon atoms, some carboxylic anhydride can be included with the carboxylic acid if desired.

Our liquid phase oxidation process produces in the case of benzene reactant conversions of the carboxylic acid in the order of 10% or greater with selectivities to the phenyl ester in the order of 100%. Thus, our process produces product in such significant quantities that it is directly competitive with the best of the present day commercial processes for the manufacture of phenyl esters and ultimately phenol itself. The phenyl ester or phenyl carboxylate product of our process can readily be converted to phenol and the corresponding carboxylic acid by known means for hydrolysis or pyrolysis. The phenol is easily recovered by known means and the carboxylic acid, ketene or acid anhydride is readily recycled for further use in the oxidation reaction of this invention.

DESCRIPTION OF THE PREFERRED EMBODIMENT

In a typical reaction in accordance with this invention a mixture of benzene and the carboxylic acid is contacted with a catalyst in an oxygen containing atmosphere at a reaction temperature in the range of from about 100° to 300° C. and preferred from 140°–200° C. and at from 1 to 100, preferably 1 to 10 atmospheres but most preferably at or near atmospheric pressure. The molecular oxygen can be oxygen, per se, or any gaseous mixture containing molecular oxygen. For instance, molecular oxygen can be in the form of air for convenience. The catalyst can be a mixture of $(CH_3COO)_2Pd$, $(CH_3COO)_3Sb$ and $(CH_3COO)_3Cr$, for instance, in molar ratio of Pd:Sb of from 1:0.1 to 1:20 and preferably 1:.1 to 1:10. The present invention represents a significant improvement over the invention of copending U.S. patent application Ser. No. 348,561 in that a chromium or other designated metal compound is also included in the catalyst in the molar ratio of from about 0.01:1 to 20:1 per mole of palladium/antimony in the catalyst. The Pd/Sb/M (wherein M is chromium cobalt, nickel, manganese, iron or tin) combination has been found by us to be unique in the sense that the components alone, i.e., Pd, Sb, or Cr or the combinations of any two components, i.e., Pd/Sb, Pd/M or Sb/M, when used for this oxidation reaction under the preferred reaction conditions resulted in much lower conversions than those obtained with the Pd/Sb/M catalyst.

During the reaction in the liquid phase, water is removed continuously as it forms and in the case in which benzene is a reactant it is continuously added and some of the benzene can be continuously removed along with the water as it forms by azeotropic distillation. In this case the major product (and in most cases the only product in addition to traces of $CO_2$), the phenyl carboxylate obtained by the process of this invention, far exceeds the best yields reported in the prior art with essentially quantitative selectivity. As previously mentioned, the phenyl carboxylate thus obtained can be hydrolyzed if so desired to produce phenol by known means and the carboxylic acid and catalyst can be recycled back to the reactor.

Because essentially no phenol is produced in the process of this invention, it is believed that catalyst activity is maintained for long periods of time under continuous use. the rapid removal of water from the reaction mixture is probably at least partly responsible for the absence of phenol in the reaction product. The presence of phenol in the reactor is believed to be responsible for catalyst fouling and short catalyst life which has been minimized in our process. The process of this invention is further demonstrated in the following illustrative examples.

EXAMPLE 1

Each of 5 experiments was conducted according to the following procedure. To a 500 ml glass reactor equipped with a mechanical stirrer, Dean-Stark type collector with condenser, thermometer and feed tubes for gas and liquid feed, there were charged octanoic acid, the Pd/Sb/Cr catalyst as acetates and benzene. The amounts of this charge are given in Table 1. The resulting mixture was stirred well and heated for 5 hours at the temperatures shown in Table 1 (140°–178° C.) while oxygen was bubbled below the surface of the mixture at a rate of 50 ml/min. The water formed as the by-product of the reaction was distilled off with benzene and collected in the Dean-Stark collector. More benzene was fed continuously but at a slow rate into the reactor during the entire course of the reaction. After the reaction had been run for 5 hours, the reaction mixture was cooled to room temperature and analyzed by GLC which showed the formation of phenyl ester of octanoic acid. The amounts of the phenyl ester formed varied depending upon the reaction temperature and are given in Table 1. It can be seen that as the temperature increased, the amount of phenyl ester also increased.

EXAMPLE 2

Six experiments were carried out exactly as in Example 1 except that the amounts of catalyst (catalyst level) were varied systematically from 2 mole% to 0.03 mole%. The reactions were carried out for 5 hours in each case, and the reaction mixtures were analyzed by GLC. Results are given in Table 2 which clearly demonstrate that as the amount of catalyst was decreased from 2 mole% to 0.06 mole%, the catalytic turnover numbers increased. This suggests that the part of the catalyst at higher catalyst level was ineffective in catalysis, i.e., was not being used. Thus, various levels of catalyst may be used according to the need.

EXAMPLE 3

This set of ten experiments were carried out exactly as in Example 1 except that the ratios of Pd/Sb/Cr were varied in order to demonstrate the wide range as well as its effect on the reaction rate. All these reactions were carried out for 5 hours and the products were analyzed by GLC. Catalytic turnover numbers as high as 90.4 were achieved. The results are given in Table 3.

TABLE 1

Temperature Effect on the Acyloxylation of Benzene in Carboxylic Acid Using Pd/Sb/Cr Catalyst. Reaction Time - 5 hrs.

| Experiment | Catalyst Composition (moles) | | | Octanoic Acid (moles) | Benzene (moles) | Reaction Temp. (°C.) | Phenyl Ester Produced | | % Conv. of Octanoic Acid |
| --- | --- | --- | --- | --- | --- | --- | --- | --- | --- |
| | Pd (OAc)$_2$ | Sb (OAc)$_3$ | Cr (OAc)$_3$ | | | | Milli-moles | Moles Product/ Mole Catalyst (T.N.) | |
| 1 | 0.006 | 0.006 | 0.006 | 0.276 | 0.250 | 140 ± 1 | 18 | 3 | 6.5 |
| 2 | 0.006 | 0.006 | 0.006 | 0.276 | 0.256 | 150 ± 2 | 68 | 11.3 | 24.6 |
| 3 | 0.003 | 0.003 | 0.003 | 0.301 | 0.258 | 160 ± 2 | 43 | 14.3 | 14.3 |
| 4 | 0.003 | 0.003 | 0.003 | 0.313 | 0.281 | 170 ± 2 | 66 | 22.0 | 21.1 |
| 5 | 0.003 | 0.003 | 0.003 | 0.321 | 0.265 | 178 ± 1 | 82 | 27.3 | 25.5 |

TABLE 2

Effect of Catalyst Level on Acyloxylation of Benzene at Temp. 160-180° C. Using Pd/Sb/Cr Catalyst. Reaction Time = 5 hrs.

| Experiment | Catalyst (m moles) | | | Octanoic Acid (m moles) | Benzene (m moles) | Reaction Temp. (°C.) | Phenyl Ester | | Mole (%) Catalyst (Pd) | % Conv. of Octanoic Acid |
| --- | --- | --- | --- | --- | --- | --- | --- | --- | --- | --- |
| | Pd (OAc)$_2$ | Sb (OAc)$_3$ | Cr (OAc)$_3$ | | | | (m moles) | Moles Prod./ Moles Pd. (T.N.) | | |
| 1 | 6 | 6 | 6 | 276 | 253 | 160 ± 1 | 72 | 12 | 2 | 26.4 |
| 2 | 3 | 3 | 3 | 301 | 258 | 160 ± 2 | 43 | 14.3 | 1 | 14.5 |
| 3 | 1.5 | 1.5 | 1.5 | 307 | 251 | 180 ± 2 | 45 | 30 | 0.5 | 15 |
| 4 | 0.75 | 0.75 | 0.75 | 320 | 278 | 180 ± 2 | 37 | 48.8 | 0.23 | 11.7 |
| 5 | 0.37 | 1.6 | 0.39 | 610 | 450 | 178 ± 2 | 29 | 78.2 | 0.06 | 4.8 |
| 6 | 0.18 | 0.8 | 0.2 | 582 | 204 | 178 ± 2 | 11.7 | 65 | 0.03 | 2.1 |

EXAMPLE 4

This set of experiments were carried out in a similar manner as in Example 1 except that chromium was replaced with other metal salts. In a typical experiment, 6 m moles of palladium acetate, 7 m moles of antimony acetate and 0.28 m moles of nickel acetate were mixed with 276 m moles of octanoic acid in the reactor. About 5 ml of benzene was charged initially and the reaction mixture was stirred and heated to 160° C. while bubbling oxygen at a rate 50 ml/minute. Additional benzene was pumped in slowly and the reaction was carried out for 5 hrs. during which time, 220 m moles of total benzene were charged. GLC analysis showed that about 17.5% of the octanoic acid charged was converted to produce 52 m moles of the phenyl ester of octanoic acid. The catalytic turnover number was calculated to be 8.7. Results of other reactions are given in Table 4.

EXAMPLE 5

To the reactor fitted with a stirrer, thermometer, Dean-Stark tube with condenser and oxygen inlet, there were charged 300 m moles of octanoic acid, 76 m moles of naphthalene, 0.75 m moles of palladium acetate, 0.75 m moles of antimony acetate, 0.75 m moles of chromium acetate, and 10 ml of heptane. The resulting mixture was stirred and heated at 170±5° C. for 4 hrs. with oxygen passing into the reactor at a rate of 50 ml/min. The water produced was removed azeotropically with heptane and collected in the Dean-Stark tube.

Analysis of the reaction mixture after 4 hrs. showed that 64% of naphthalene was converted to produce 48 m moles of the naphthyl ester of octanoic acid.

EXAMPLE 6

TABLE 3

Effect of Varying the Pd/Sb/Cr ratios on the Acyloxylation of Benzene at Temp. 160-180° C. Reaction Time = 5 hrs.

| Experiment | Catalyst (m moles) | | | Ratio Pd/Sb/Cr | Mole % Pd | Octanoic Acid (m moles) | Benzene (m moles) | Reaction Temp. (°C.) | Phenyl Ester | | % Conv. of Octanoic Acid |
| --- | --- | --- | --- | --- | --- | --- | --- | --- | --- | --- | --- |
| | Pd (OAc)$_2$ | Sb (OAc)$_3$ | Cr (OAc)$_3$ | | | | | | (m moles) | mole prod./ mole Pd (T.N.) | |
| 1 | 6 | 6 | 12 | 1/1/2 | 2 | 276 | 250 | 160 ± 2 | 51 | 8.5 | 19 |
| 2 | 3 | 3 | 4.5 | 1/1/1.5 | 2 | 138 | 251 | 160 ± 2 | 24 | 8 | 18 |
| 3 | 6 | 6 | 6 | 1/1/1 | 2 | 276 | 259 | 160 ± 2 | 65 | 11 | 24 |
| 4 | 0.35 | 0.33 | 0.39 | 1/1/1 | 0.1 | 329 | 230 | 180 | 23 | 66 | 7.1 |
| 5 | 0.37 | 1.6 | 0.41 | 1/4.3/1.1 | 0.11 | 345 | 238 | 175 − 80 | 33.2 | 90.4 | 9.6 |
| 6 | 0.37 | 3.2 | 0.41 | 1/8.6/1.1 | 0.11 | 335 | 203 | 180 | 21.8 | 59 | 6.6 |
| 7 | 0.37 | 1.6 | 0.8 | 1/4.3/2.4 | 0.11 | 335 | 225 | 180 ± 1 | 24.1 | 64 | 7.3 |
| 8 | 0.35 | 0.8 | 0.41 | 1/2.2/1.1 | 0.1 | 351 | 220 | 180 | 21.3 | 61 | 6.2 |
| 9 | 0.35 | 0.8 | 1.7 | 1/2.3/4.4 | 0.11 | 320 | 225 | 180 | 25.1 | 71 | 8.0 |
| 10 | 0.36 | 0.8 | 0.21 | 1/2.2/0.6 | 0.12 | 311 | 168 | 180 | 15.0 | 42 | 5.0 |

TABLE 4

Effect of variation of M on Pd/Sb/M Catalyst in Octanoic Acid at 160° C. Reaction Time = 5 hrs.

| Experiment | Catalyst (m moles) Pd | Sb | M | Octanoic Acid (m moles) | Benzene (m moles) | Reaction Temp. (°C.) | Phenyl Ester (m moles) | Mole prod./ mole Pd (T.N.) | % Conv. of Octanoic Acid |
|---|---|---|---|---|---|---|---|---|---|
| 1 | 6 | 6 | Cr 6 | 276 | 259 | 160 ± 2 | 65 | 11 | 24 |
| 2 | 6 | 7 | Ni 0.28 | 276 | 220 | 160 | 52 | 8.7 | 17.5 |
| 3 | 6 | 6 | Mn 6 | 276 | 205 | 160 | 28 | 4.6 | 10.0 |
| 4 | 6 | 6 | Fe 6 | 276 | 187 | 160 ± 1 | 42 | 7 | 16 |

This set of experiments were carried out exactly as in Example I except that various other carboxylic acids were used instead of octanoic acid. The results of these experiments are given in Table 5.

EXAMPLE 7

To a 500 ml reactor equipped as in Example 1, was charged 1128 m moles of octanoic acid, 3 m moles of palladium acetate, 3 m moles of antimony acetate, 3 m moles of chromium acetate and 10 ml of benzene. The reaction mixture was stirred and heated at 170°–5° C. while adding oxygen at a rate of 75 ml/minute. The reaction was carried out for 24 hrs. and additional benzene was fed slowly during the course of the reaction. The total benzene introduced was about 700 m moles. Samples of the reaction mixture were withdrawn at various time intervals and analyzed by GLC. The results which are given below clearly demonstrate a continuous production of phenyl esters.

| Reaction Time (hrs) | wt % Phenyl Ester | Reaction Time (hrs) | wt % Phenyl Ester |
|---|---|---|---|
| 2 | 8 | 12 | 27 |
| 3 | 12.4 | 15 | 30 |
| 6 | 18.5 | 18 | 32.3 |
| 9 | 23 | 24 | 38.5 |

EXAMPLE 8

Experiments were conducted in a high pressure reactor equipped with either a built-in high-pressure condenser or a high-pressure condenser connected to a reactor at the outside. Typically, the reactor was charged with 208 m moles of octanoic acid, 0.5 m moles of palladium acetate, 0.5 m moles of antimony acetate, 0.5 m moles of chromium acetate and 100 m moles of benzene. The reactor was pressurized to 20 psig with oxygen. The reaction mixture was stirred and heated at 170°±5° C. The atmosphere of the reactor was continuously vented and pressurized with fresh oxygen. The reaction was carried out for 4 hrs. and the analysis showed that 7 m moles of phenyl ester were produced. The catalytic turnover numbers were calculated to be 14.

TABLE 5

Use of Various Carboxylic Acids in the Acyloxylation of Benzene Using Pd/Sb/Cr Catalyst. Reaction Time = 5 hrs.

| Experiment | Catalyst (m moles) Pd (OPc)$_2$ | Sb (OAc)$_3$ | Cr (OAc)$_3$ | Carboxylic Acid (m moles) | Benzene (m moles) | Reaction Temp. (°C.) | Phenyl Ester (m moles) | mole Prod./ mole Pd (T.N.) | % Conv. Carboxylic Acid |
|---|---|---|---|---|---|---|---|---|---|
| 1 | 3 | 3 | 3 | Lauric Acid 552 | 648 | 175 ± 1 | 34 | 11.3 | 15 |
| 2 | 3 | 3 | 3 | *DDA 276 | 245 | 160 ± 1 | 27 | 9 | 10 |
| 3 | 6 | 6 | 6 | Adipic Acid 180 | 180 | 155 ± 5 | 12 | 2 | 4.5 |
| 4 | 6 | 6 | 6 | 2-Ethyl Hexanoic Acid 276 | 195 | 158 ± 2 | 11 | 2 | 4.0 |

*Dodecanedioic Acid

We claim:

1. An oxidation process for the manufacture of aryl esters consisting of contacting a reaction mixture of an aromatic compound selected from the group consisting of benzene, naphthalene, anthracene, phenanthrene, biphenyl and terphenyls, a carboxylic acid and molecular oxygen in the liquid phase at a temperature in the range of 100° to 300° C. with a catalyst composed of palladium acetate an antimony acetate and an acetate of at least one member selected from the group consisting of chromium and manganese, and removing continuously the water formed in the process from the reaction mixture as the aryl ester is formed.

2. The process of claim 1 wherein the carboxylic acid has the formula R (COOH)$_n$ wherein n is an integer of 1 or more and R is a hydrocarbon group having at least 5-n carbon atoms, wherein the aromatic compound is added continuously to the reaction mixture as the aryl ester is formed.

3. The process of claim 2 wherein the aromatic compound is benzene.

4. The process of claim 3 wherein the palladium compound is palladium acetate.

5. The process of claim 4 wherein the antimony compound is antimony acetate.

6. The process of claim 5 wherein the chromium compound is chromium acetate.

7. The process of claim 6 wherein the carboxylic acid is dodecanedioic acid.

8. The process of claim 5 wherein the carboxylic acid is octanoic acid.

9. The process of claim 5 wherein the nickel compound is nickel acetate.

10. The process of claim 5 wherein the manganese compound is manganese acetate.

* * * * *